(12) United States Patent
Marsden et al.

(10) Patent No.: US 8,387,461 B2
(45) Date of Patent: Mar. 5, 2013

(54) INSPECTION METHOD

(75) Inventors: John Nicholas Marsden, Aberdeen (GB); Stuart Andrew Mitchell, Ellon (GB)

(73) Assignee: Flexlife Limited, Aberdeen (GB)

( * ) Notice: Subject to any disclaimer, the term of this patent is extended or adjusted under 35 U.S.C. 154(b) by 190 days.

(21) Appl. No.: 12/668,603

(22) PCT Filed: Jun. 12, 2008

(86) PCT No.: PCT/GB2008/002000
§ 371 (c)(1),
(2), (4) Date: Jun. 11, 2010

(87) PCT Pub. No.: WO2009/007670
PCT Pub. Date: Jan. 15, 2009

(65) Prior Publication Data
US 2011/0113884 A1    May 19, 2011

(30) Foreign Application Priority Data

Jul. 11, 2007   (GB) .................................. 0713396.0

(51) Int. Cl.
*G01N 29/04*    (2006.01)
(52) U.S. Cl. ........................................... 73/623; 73/602
(58) Field of Classification Search .............. 73/623, 73/768, 783, 847, 40.5 R, 49.5
See application file for complete search history.

(56) References Cited

U.S. PATENT DOCUMENTS

| | | | |
|---|---|---|---|
| 3,810,384 A | 5/1974 | Evans | |
| 4,144,517 A | 3/1979 | Baumoel | |
| 4,432,931 A * | 2/1984 | Lockett | 376/248 |
| 4,775,855 A * | 10/1988 | Cox | 340/605 |
| 5,329,561 A | 7/1994 | Desruelles | |
| 5,456,108 A | 10/1995 | Birkett | |
| 5,463,905 A | 11/1995 | Baird | |
| 5,982,839 A * | 11/1999 | Hatley | 376/245 |
| 6,171,025 B1 * | 1/2001 | Langner et al. | 405/154.1 |
| 6,536,283 B1 * | 3/2003 | Hatley | 73/622 |
| 6,814,146 B2 * | 11/2004 | Bass et al. | 166/302 |
| 7,296,480 B2 * | 11/2007 | De Aquino | 73/847 |
| 2004/0173021 A1 | 9/2004 | Lizon et al. | |

FOREIGN PATENT DOCUMENTS

| | | |
|---|---|---|
| EP | 0 415 848 A | 3/1991 |
| JP | S60-174948 | 9/1985 |
| JP | 5188041 | 7/1993 |
| JP | 8054227 | 2/1996 |
| JP | 3205555 | 7/2001 |
| JP | 2001201388 JP | 7/2001 |

(Continued)

OTHER PUBLICATIONS

Notification Concerning Transmittal of International Preliminary Report on Patentability for International Application No. PCT/GB2008/002000 (Jan. 21, 2010).

(Continued)

*Primary Examiner* — J M Saint Surin
(74) *Attorney, Agent, or Firm* — Jenkins, Wilson, Taylor & Hunt, P.A.

(57) ABSTRACT

A method of monitoring the condition of a flexible pipeline comprising the step of scanning the pipeline with an ultrasonic scanner to produce and/or record a signal indicative or the level of flooding within the annulus of the pipeline and/or indicative of the integrity of the layers of the pipeline.

8 Claims, 2 Drawing Sheets

FOREIGN PATENT DOCUMENTS

RU            2 153 602 C1     7/2000

OTHER PUBLICATIONS

International Search Report for International Application No. PCT/GB2008/002000 (Sep. 15, 2008).

Baltzersen et al., "Internal Ultrasonic Inspection of Flexible Pipe," NDT&E International UK, vol. 26, No. 5, p. 241-248 (Oct. 1993).

De Oliveira Carneval et al., "Flexible Line Inspection," ECNDT 2006—Poster 106, pp. 1-11 (2006).

Out et al., "The Integrity of Flexible Pipe: Search for an Inspection Strategy," Engineering Structures, vol. 17, No. 4, pp. 305-314 (1995).

Hawker, "NDT of Flexible Risers, A Safety Review for HOIS," AEAT-3260, HOIS(98)P4m, Issue 2.1 (Jan. 1999).

Leonard, "New Developments in Flooded Member Detection," Advances in Underwater Technology, Ocean Science and Offshore Engineering, vol. 14 Submersible Technology, pp. 257-263 (1988).

Povey et al., "Ultrasound in Food Processing: Rapid determination of food material properties," pp. 30-65 (1998).

Baker et al., "Reliability-based methods in the inspection planning of fixed offshore steel structures," Journal of Constructional Steel Research, pp. 117-131 (1999).

Morris, "Measurement and Instrumentation Principles," pp. 259-260 and 344-345 (2001).

Notice of Opposition in UK Patent No. 2446670 (Mar. 18, 2011).

Counter statement filed by Proprietor in Opposition of UK Patent No. 2446670 (Jan. 5, 2012).

Letter filed by Opponent in Opposition of UK Patent No. 2446670 (Jul. 18, 2012).

Submission of Evidence by Proprietor in Opposition of UK Patent No. 2446670 (Sep. 12, 2012).

Decision for UK Patent No. GB2446670B (Jan. 2, 2013).

\* cited by examiner

INSPECTION METHOD

This invention relates to an inspection method and more specifically to a method of inspecting a flexible pipeline. More particularly, the invention relates to a method of inspecting the integrity of an annulus of a flexible pipeline.

Flexible Pipe is a term used to describe a multi-layered pipe, which is formed from materials, which allow it to bend relatively easily. It is generally constructed of various layers of materials such as polymers and metals or composites.

Flexible pipes are used throughout the oil and gas industry both onshore, and predominately offshore. Their attraction is the ease of installation and their ability to withstand cyclic bending, and therefore they are less prone to fatigue than rigid risers.

FIGS. 1 and 2 show part cross-sections through two typical flexible pipe constructions.

The flexible pipe of FIG. 1 is a rough bore flexible pipe, which comprises an inner carcass 1 generally formed of interlocked wires, which provides stability to the pipeline and resists collapse of the construction. Surrounding the carcass is a pressure sheath 2, which is generally formed by a thermoplastic inner fluid barrier and provides a seal to prevent internal fluid flowing in the pipeline from escaping from the inner carcass.

A pressure armour 3 is formed around the outer surface of the pressure sheath and provides hoop strength to the pipeline to prevent collapse.

A helically wound tensile armour 4 formed of rectangular or round wire or composite rods is provided over the pressure armour to provide axial support and to support the hoop strength of the pipeline. A wear layer 5 of thermoplastic or tape overlies the tensile armour 4 and limits the steel layer wear by reducing the contact forces and abrasion thereon. The wear layer 5 also constrains the wires and acts as a manufacturing aid.

In the example shown, a further tensile armour 4' is applied over the wear layer 5 and followed by a thermal insulation layer 6 which reduces heat loss from the pipeline. An outer sheath 7 surrounds the inner layers, said outer sheath being formed of a thermoplastic, which provides environmental protection and prevents seawater ingress into the pipeline.

FIG. 2 shows a typical construction for a smoothbore flexible pipe which is formed of an inner liner 8 of thermoplastics, which provides an inner fluid barrier without the requirement for an internal carcass, surrounded by a pressure armour 3 as described in relation to FIG. 1. Surrounding the pressure armour 3 is an intermediate seal 9, which is formed from a thermoplastic hydrostatic pressure barrier, which allows the pressure armour 3 to resist hydrostatic load when the outer sheath 7 is breached as discussed further below.

A tensile armour 4 surrounds the intermediate seal over which a wear layer 5 and further tensile armour 4' are provided. Finally the outer sheath 7 surrounds the preceding layers as described above.

In some cases, a further thermoplastic extrusion (not shown) may be provided over the outer sheath 7 to protect the outer sheath 7 from loads and abrasion and an external carcass (not shown) may surround the entire pipeline to protect the sheath 7 from loads, abrasion and impact damage, particularly where the pipeline is laid on the sea bed.

Flexible pipes are usually constructed using the layers listed above and can comprise multiples of these layers depending on the application The annulus of the pipe, the pressure armour 3 and tensile armour 4, 4' layers are of particular interest in relation to the present invention. The annulus is the space between the outer sheath 7 and an internal sealing layer such as the internal pressure sheath 2, 3, liner, or intermediate seal 9. The tensile and pressure armour layers are the outer wires, which withstand as their name suggests the tensile loads and pressure induced loads of the pipe and are located within the annulus.

The fatigue resistance of a flexible pipe is significantly reduced when the tensile armour 4, 4' or pressure armour 3 wires of a pipe are exposed to seawater, corroded, or damaged.

In each flexible pipe configuration, the flexible pipe annulus condition is critical to the service life and performance of the pipe. This becomes more important the more dynamic the pipe. Typically, Risers and Dynamic Jumpers are much more sensitive to fatigue than Flowlines and Static Jumpers.

The annulus can be flooded through either seawater ingress or permeated fluid from the bore. In either case this environment reduces the design service life of the pipe. Monitoring this condition is therefore a key factor in prediction of service life and assessment of flexible pipe assets offshore. Failure to monitor the annulus environment can lead to loss of containment of the pipe's contents and cause serious environmental damage, injury, fatality, or even total loss of the offshore platform to which the flexible pipe is connected.

Presently, only pipes where an end termination, which secures each flexible pipe layer, is accessible permit the monitoring of the annulus condition. The annulus investigation usually relies upon user interrogation to assess the annulus. This operation is normally carried out during the pipe shut down and part of planned preventative maintenance.

There are presently two common methods of monitoring the condition of the annulus of a pipe; positive pressure testing and vacuum testing.

In the first case, this requires the pipe to be shut down and typically takes 12-16 hours per test. The principle is based on the 'combined gas law' which is a gas law that combines Charles's Law, Boyle's Law, and Gay-Lussac's Law: "The product of the volume of a gas and its pressure over the temperature is equal to a constant." Simply:

$$\frac{P_1 V_1}{T_1} = \frac{P_2 V_2}{T_2}$$

In order to accurately perform this test the original annulus volume ($V_1$) must be known, this should be recorded in the factory during the acceptance testing of the pipe. Often this is not performed and therefore use of this method is not very accurate.

With the second test, the pipe must also be shut down for the test to be carried out which typically takes 12-16 hours per test. The annulus vent system is isolated to draw a partial vacuum in the annulus space. Annulus pressure is reduced gradually over a 12 hour period until a pressure of 250 mbara is achieved. The vacuum is considered stable when the pressure increase does not exceed 10% over a 1 hour period after reaching 250 mbara annulus pressure. The test is a pass when the pressure increase in the annulus does not exceed 10% of the annulus pressure at the start of the 1 hour period after reaching 250 mbara annulus pressure. A flooded annulus will have a greatly reduced volume and therefore takes less time to pull the vacuum. This test can use calculation to derive the theoretical annulus volume, this is an inaccurate method of deriving the volume.

Both tests to evaluate the condition of the annulus take many hours to complete and rely on the pipes being shut down to perform. This is a costly exercise especially where there may be many flexible pipes to test or if a flexible is the main export pipe; say for a facility producing 150,000 barrels a day at $40 a barrel that is approximately $3M. It is easy to see how costs could preclude this type of necessary testing.

The actual volume evaluated can be prone to inaccuracies especially if the annulus volume was not requested by the customer at manufacture. There is therefore the potential for a pipe to be deemed not flooded in partial flooded cases and subsequently fail due to inaccuracies of the test. There is a safety concern regarding these tests, the annulus can contain permeated gases such as $H_2S$, or hydrocarbons, these pose a risk to the technician and the asset the flexible pipe is connected to.

Even where the tests discussed above show that the annulus is flooded, neither allow the operator to assess the condition of the tensile armour or pressure armour wires. Indeed there is no reliable method of evaluating this other than calculating the corrosion due to annulus environment. Methods such as x-ray are difficult to use reliably due to the layered construction of the flexible, not to mention the safety aspects regarding the source required for this type of testing.

Intelligent pigging of flexible pipes has been attempted without much success again mainly due to the multi-layered construction and the time required to build up comprehensive picture make this test too expensive.

The present invention aims to provide an inspection method, which overcomes or at least mitigates the aforementioned problems in monitoring the integrity of the annulus of a pipeline.

According to one aspect of the present invention there is provided a method of monitoring the condition of a flexible pipeline comprising the step of scanning the pipeline with an ultrasonic scanner.

Preferably the method includes the step of producing and/or recording a signal indicative of the level of flooding within the annulus of the pipeline.

Preferably also, the method includes the step of producing and/or recording a signal indicative of the integrity of the layers of the pipeline.

Advantageously, the signals representing the level of flooding within the annulus and the integrity of the layers of the pipeline are simultaneously obtained.

Preferably the method further comprises the step of displaying results of the scan on a display apparatus.

Advantageously, the results of the scan are displayed in real time during the scanning process.

Conveniently the method further comprises the step of deploying an ROV from a surface facility, said ROV carrying apparatus for scanning the pipeline in situ.

Preferably the scanning process is controlled from a location remote from the pipeline.

The term "flexible pipeline" includes (but is not limited to) all flexible flowlines, flexible pipes and flexible risers. Flexible flowline is generally used to refer to flexible pipe that at least partially rests on the seafloor or is buried on the seabed. Flexible pipe typically refers to a pipe body comprising a composite of layered materials that form a pressure-retaining conduit. Flexible risers are generally flexible pipes connecting a platform, buoy or ship to a flowline, seabed installation, or other platform. The riser may be freely suspended or in a catenary configuration. Alternatively, it may be restrained to some extent using buoys or chains or totally restrained or enclosed in a tube.

An embodiment of the present invention will now be described by way of example only with reference to the accompanying drawings in which: —

As described above, the cross section of a typical flexible pipe is made up of helically wound wires or composites and tapes. This amalgamation of wires and tapes is not easy to inspect with current technology as discussed. The present invention provides a method of inspecting the pipeline and particularly the pipe annulus for problems such as flooding.

Figure 1:
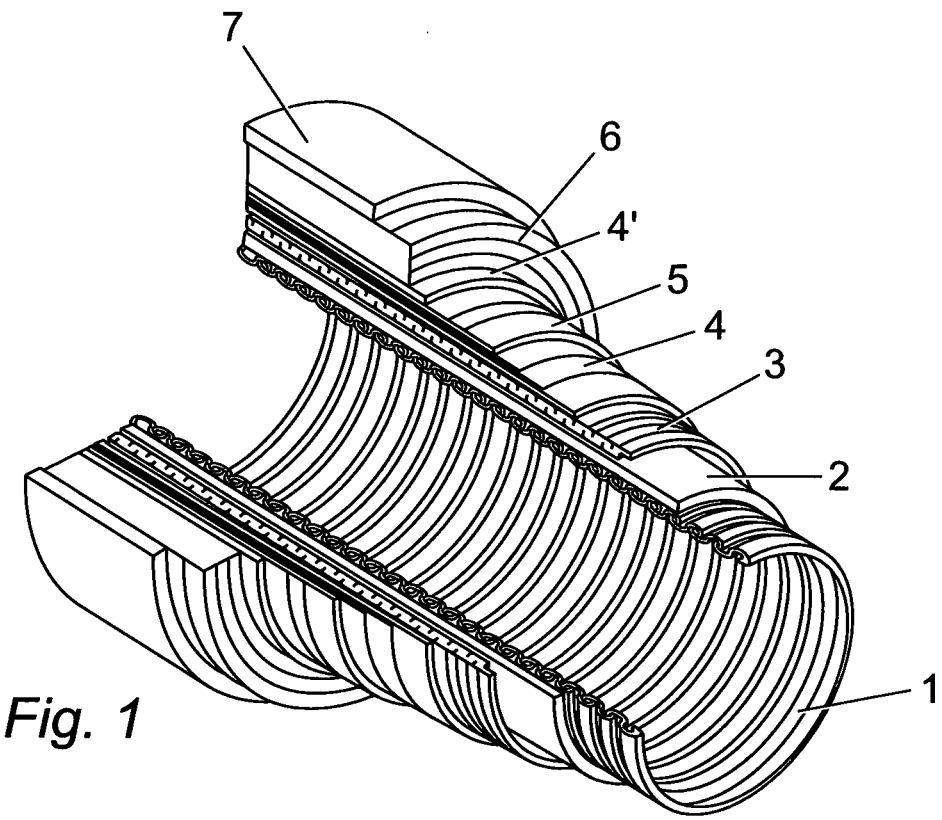
FIG. 1 is a part cross-sectional view of a typical construction of a rough bore flexible pipeline.
Figure 2:
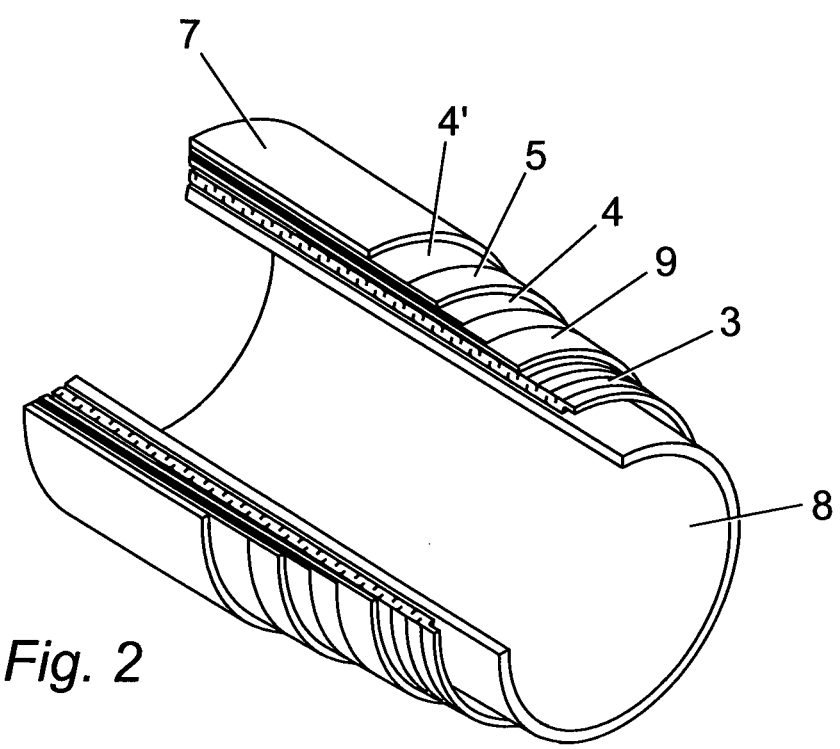
FIG. 2 is a part cross-sectional view of a typical construction of a smoothbore flexible pipeline.
Figure 3:
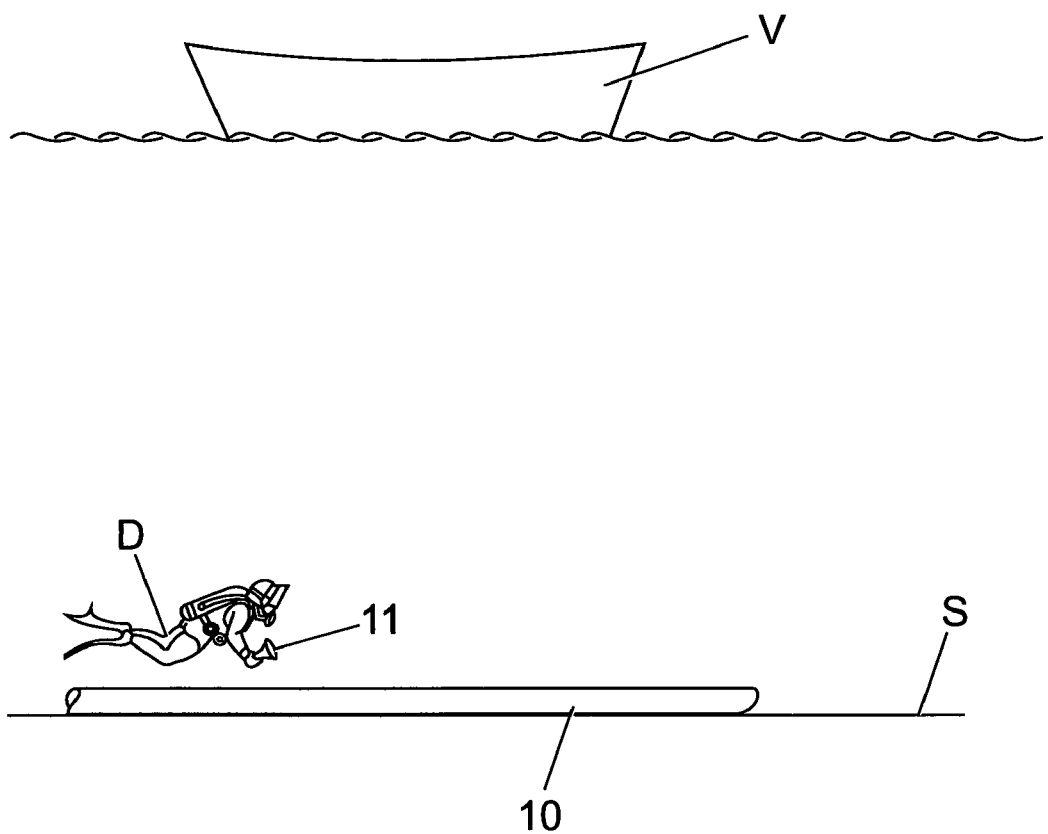
FIG. 3 is a schematic view illustrating a scanning operation according to one aspect of the present invention.

In the example shown in FIG. 3, a flexible pipeline 10 lies on the seabed S and may be used for example to carry hydrocarbons from a seabed drilling facility to a shore based processing plant.

In order to determine the condition of a section of the pipeline, a diver D is deployed from a surface vessel or platform V with a handheld ultrasonic scanner 11 to the seabed. Display apparatus (not shown) is provided on the surface vessel to receive signals from the scanner and to display the resulting signals in graphic form.

The diver scans the surface of the pipeline 10 at selected intervals along the section to be inspected. The speed of sound travels through various mediums at different rates and therefore an ultrasound scan will reflect the signal passing through air and water at different rates. The signal received by the ultrasound scanner provides a three-dimensional image of the pipeline. This will identify a flooded annulus without having to resort to the drastic measures described above in relation to prior art monitoring methods.

Furthermore, the scan will also provide information as to the depth of the water in the annulus. This is a significant development as it allows the required remedial work to be undertaken at the most opportune time and in many cases, will allow remedial work to be undertaken before the flooding in the annulus reaches a critical level. Resources can then be better directed to prioritising remedial work where it is most required.

In addition, the ultrasound scan will provide an indication as to the level of corrosion of specific layers or wires within the pipe annulus due to the wires being of different materials, through each of which the speed of sound is slightly different. By interpreting the results of the scan, an accurate picture of the status of the various layers of the pipeline can be built up and decisions taken based upon accurate information as to the status of the pipeline.

In each case, the invention provides a fast, accurate and cost effective method of annulus condition monitoring. Specifically the method is non-invasive and the pipes do not require a shut down in order to inspect, this will undoubtedly increase the number of inspections throughout the pipe's service life and lead to increased reliability.

In subsea environments, the scanning operation can be carried out by divers using hand held scanning equipment as described above or alternatively, a remotely operated vehicle (ROV) may be used for scanning operations in deep water situations such as for example where the safety of divers may be compromised. Optionally, pigs with ultrasonic capability may be used in the throughbore of the pipeline of interest. For example, ultrasonic pigging is especially useful for flexibles that are difficult to reach or inaccessible to divers and/or ROVs.

According to other embodiments, the method can be conducted on other flexibles, such as flexible risers typically extending from the seabed to surface. Additionally, flexible risers can be inspected directly from a platform. The method of the invention is advantageous for the inspection of risers, since the previously mentioned positive pressure testing is only possible where risers have topside vent ports that can be subject to vacuum or positive pressure testing to assess annulus condition.

Furthermore, the method of the invention obviates the need for a separate corrosion inspection of the tensile armour 4. The ultrasonic data enables a corrosion integrity assessment of the steel wires making up the flexible riser/flowline to be conducted by performing a pattern recognition of the tensile armour 4 by scanning a number of wires. This data will enable a person skilled in the art to determine the level of corrosion for the wires scanned. Typically, in order to obtain information regarding the state of the flexible line at least two separate integrity surveys are carried out: a pressure test of the annulus; and a further X-ray or laser tomography assessment for corrosion monitoring. The ultrasonic data from the method of the invention provides information to enable corrosion monitoring of the tensile armour 4 (and other steel wire components) as well as annulus condition monitoring. Therefore, the invention represents an advantage in terms of reducing the number and cost of inspecting flexibles using the ultrasonic technique.

It is envisaged that the results of the scanning operation will be transmitted to a display apparatus such as a microprocessor on a surface vessel or other surface facility. This will allow the scanning operation to be directed using real time information as to the integrity of the pipeline.

Alternatively, the results of the scanning operation may be saved locally in the scanner and downloaded at a surface facility for interpretation.

Whilst the invention has been described in relation to subsea use, it is to be understood that it may also be used in onshore operations.

What is claimed is:

1. A method of monitoring the condition of a flexible pipeline comprising the steps of scanning the pipeline with an ultrasonic scanner and producing and/or recording a signal indicative of the level of flooding within the annulus of the pipeline and using the information provided from the signal to determine the level of flooding within the annulus and to identify a flooded section of the flexible pipeline.

2. A method according to claim 1, wherein the method includes the step of producing and/or recording a signal indicative of the integrity of the layers of the pipeline.

3. A method according to claim 2, wherein the signals representing the level of flooding within the annulus and the integrity of the layers of the pipeline are simultaneously obtained.

4. A method according to claim 1, wherein the method further comprises the step of displaying results of the scan on a display apparatus.

5. A method according to claim 4, wherein the results of the scan are displayed in real time during the scanning process.

6. A method according to claim 1, wherein the method further comprises the step of deploying an ROV from a surface facility, said ROV carrying apparatus for scanning the pipeline in situ.

7. A method according to claim 1, wherein the scanning process is remotely controlled.

8. A method according to claim 1, wherein the scanning process is controlled from a location remote from the pipeline.

* * * * *